United States Patent [19]

Pariza et al.

[11] Patent Number: 5,070,104

[45] Date of Patent: Dec. 3, 1991

[54] METHODS OF CHELATING METAL AND NOVEL COMPOSITIONS THEREFOR

[75] Inventors: Michael W. Pariza; Yeong L. Ha, both of Madison, Wis.

[73] Assignee: Wisconsin Alumni Research Foundation, Madison, Wis.

[21] Appl. No.: 474,583

[22] Filed: Feb. 2, 1990

Related U.S. Application Data

[63] Continuation-in-part of Ser. No. 313,120, Feb. 17, 1989, Pat. No. 5,017,614.

[51] Int. Cl.$^5$ ....................... A61K 31/22; A61K 31/20
[52] U.S. Cl. .................................. 514/549; 514/560; 424/DIG. 6
[58] Field of Search ..................... 514/552, 560, 549; 424/DIG. 6

[56] References Cited

U.S. PATENT DOCUMENTS

| | | | |
|---|---|---|---|
| 4,215,144 | 7/1980 | Thiele | 514/560 |
| 5,017,614 | 5/1991 | Pariza et al. | 514/558 |

OTHER PUBLICATIONS

Y. L. Ha, N. K. Grimm and M. W. Pariza, in Carcinogenesis, vol. 8, No. 12, pp. 1881–1887 (1987).
Y. L. Ha, N. K. Grimm and M. W. Pariza, in J. Agric. Food Chem., vol. 37, No. 1, pp. 75–81 (1987).
Osawa and Namiki (Agric. Biol. Chem. 45: pp. 735–739, 1981).
Pariza, Food Research Institute 1988 Annual Fall Meeting, Oct. 12, 1988.
Science News, vol. 135, No. 6, p. 87 (1989).
Barry Halliwell, Oxidants and Human Disease: Some New Concepts, FASEB J. 1: 358–364; 1987.
K. M. Schaich and D. C. Borg, Fenton Reactions in Lipid Phases, Lipids, vol. 23, No. 6; 570–579 (1988).

*Primary Examiner*—Frederick E. Waddell
*Assistant Examiner*—Raymond J. Henley, III
*Attorney, Agent, or Firm*—Quarles & Brady

[57] ABSTRACT

A method of chelating a metal in solution comprise adding to the solution a safe and effective amount of an active form of CLA. Pharmaceutical preparations for practice of the method in vivo are disclosed.

6 Claims, No Drawings

METHODS OF CHELATING METAL AND NOVEL COMPOSITIONS THEREFOR

This invention was made with U.S. Government support awarded by the National Institutes of Health (NIH), Grant Nos.: NIH-NIEHS T32-ES-0715. The U.S. Government has certain rights in this invention.

RELATED CASE

This application is a continuation-in-part of U.S. Pat. application Ser. No. 07/313/120, filed Feb. 17, 1989, now U.S. Pat. No. 5,017,614.

FIELD OF THE INVENTION

The present invention relates generally to methods and compositions for chelating iron and other metals. It also relates to novel parenteral compositions and a method of chelating metals in vivo.

BACKGROUND OF THE INVENTION

Among the more widely used metal chelators is the compound ethylene diaminetetraacetic acid (EDTA). EDTA is used in industry and in food products because it is relatively non-toxic. However, it is not a naturally occurring compound. Therefore, it cannot be used in "natural" food products.

There is a need for a metal chelator which can be used in "natural foods."

Calcium disodium edeate, a salt of EDTA, has been used in medicine to treat lead and cadmium poisoning. Penicillamine also has been used as a chelating agent in medicine. Neither EDTA or penicillamine are believed to be effective in chelating iron in vivo. It would be helpful to have a natural chelating agent for iron as it is believed that the effective chelation of iron in vivo could be of great value in the inhibition of membrane peroxidation. Such chelation could prevent the occurrence of Fenton-type reactions and subsequent damage by hydroxyl radicals of membrane sites that are involved in the induction of various pathological conditions, including the initiation of carcinogenesis.

There is a need for safe and effective methods of chelating metals, such as iron, in vivo and a need for safe and effective compositions for use in such methods.

SUMMARY OF THE INVENTION

The primary object of the present invention is to disclose safe and effective methods of chelating metals using a naturally occurring chelator.

A further object is to disclose novel pharmaceutical compositions for use in methods of chelating metals in vivo.

The methods of the present invention may take several embodiments. In one embodiment, the chelating agent is added to a solution containing the metal to be chelated. And, in a second embodiment, the chelating agent is formed in situ in the solution containing the metal. For example, in one embodiment the chelating agent could be administered to an animal in a pharmaceutical composition containing a safe and effective dose of the chelating agent. And, in the second embodiment the animal could be fed a safe amount of the reactants necessary to form the chelating agent in situ.

The chelating compositions of the present invention are those containing the free conjugated linoleic acids (CLA) 9,11-octadecadienoic acid and 10,12-octadecadienoic acid. Active forms of CLA also include compositions containing the active isomers of CLA; non-toxic salts thereof; active esters and other active chemical derivatives thereof; and mixtures thereof.

The free conjugated linoleic acids (CLA) have been previously isolated from fried meats and described as anticarcinogens by Y. L. Ha, N. K. Grimm and M. W. Pariza, in Carcinogenesis Vol. 8, No. 12, pp. 1881–1887 (1987). Since then, they have been found in some processed cheese products. Y.L. Ha, N. K. Grimm and M. W. Pariza, in J. Agric. Food Chem., Vol. 37, No. 1, pp. 75–81 (1987). However, parenteral pharmaceutical preparations containing CLA, or the non-toxic salts, such as the sodium and potassium salts, in combination with sterile water for injection are novel.

The free acid forms of the compositions of the present invention (CLA) are preferably prepared by reacting linoleic acid with a protein, such as whey protein, which is capable of effecting the transformation of linoleic acid to the desired compositions at temperatures up to about 85° C. The non-toxic salts of the free acids may be made by reacting the free acids with a non-toxic base. Natural CLA may also be prepared from linoleic acid by the action of $\Delta^{12}$-cis, $\Delta^{11}$-transisomerase from a harmless microorganism such as *Butyrivibrio fibrisolvens*.

Triglyceride esters may be prepared by reacting a triglyceride containing linoleic acid, such as corn oil, with a protein capable of effecting the transformation of linoleic acid to the active material, such as whey protein. Similar methods can be used to prepare other esters, such as methyl or ethyl esters.

A form of CLA suitable for use in "natural" foods is preferably prepared by reacting roughly equivalent amounts of a natural source of linoleic acid, such as butter fat, with milk whey protein at ambient temperatures. The reaction proceeds quickly even when the ingredients are simply intimately mixed.

While any source of linoleic acid can be used to prepare CLA, the highest yields are obtained when a source rich in linoleic acid, such as corn oil or safflower oil, are used.

The preferred protein which is used to transform linoleic acid to an active form of CLA is whey protein which contains sulfhydryl groups and is, of course, readily available. Other proteins that will transform linoleic acid to CLA can be readily determined without undue experimentation by those skilled in the art. Among such proteins would be those that contain sulfhydryl groups, as well as, non-sulfhydryl containing proteins.

The CLA obtained by the practice of the preferred method of preparation contains one or more of the 9,11-octadecadienoic acids and/or 10,12-octadecadienoic acids and active isomers thereof It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

CLA and its active non-toxic derivatives, such as the non-toxic salts, can be administered in the form of pharmaceutical compositions, such as tablets, capsules, solutions or emulsions to animals, including humans, to chelate metals, such as iron, in vivo. The exact amount to be added, of course, depends upon the form of CLA employed, the amount of metal to be chelated and the nature of the patient's condition or disease. Generally, the amount employed of CLA and its non-toxic salts will range from about one part per million (ppm) to about 1,000 ppm of CLA. The amount to be employed is not critical as long as it is sufficient because CLA is relatively non-toxic and it is a normal constituent of the human diet (including human breast milk).

The exact mechanisms by which the CLA acts as a metal chelator is not known. A possible mechanism of action for the CLA is that a novel diketone structure, which can chelate metals, such as iron, forms when the CLA is exposed to oxygen. The diketone could result from the reaction of molecular oxygen and activated oxygen species with the conjugated double bond system of CLA. The mechanism by which CLA chelates iron might then be similar to that of other chelating diketones. It is also possible that the native unaltered form of CLA may chelate transition metals.

The following examples illustrate the preparation of the CLA by the method of the invention, and the use of CLA to chelate iron.

EXAMPLE 1

Preparation of CLA

Forty grams of whey protein and forty five grams of a fat source containing linoleic acid (butter fat) were intimately mixed at ambient temperature and then pasteurized at 85° C. for 5 minutes. After 30 minutes the mixture was assayed for CLA as previously described. The CLA thus formed was stable at 25° C. for up to 8 weeks (See FIG. 2).

EXAMPLE 2

Preparation of Potassium Salt

The potassium salt of CLA was prepared by adding about 50 g. of CLA to 100 ml of water, adjusting to pH 8.5 with 1N KOH, and freeze drying. The resulting product was a white powder.

EXAMPLE 3

Preparation of Sodium Salt

The sodium salt of CLA was prepared by adding about 50 g. of CLA to 100 ml of water, adjusting to pH 8.5 with 1N NaOH, and freeze drying. The resulting product was a white powder.

EXAMPLE 4

Chelation of Iron

10 $\mu$moles free CLA or CLA methyl ester is 2 ml ethanol is added to a reaction mixture containing 2 emoles of ferrous iron ion ($Fe^{+2}$) in 50 ml Tris buffer (0.05 M, pH 7.7). The mixture is stirred. After 1 and 18 hours the amount of iron in the aqueous portion was diminished by 0% and 84% (with free CLA), or 17% and 37% (with CLA methyl ester), respectively.

EXAMPLE 5

Chelation of Lead 0.28 mg of CLA is added to a solution containing lead chloride (0.1 $\mu$M) in 100 ml Tris buffer (0.05 M, pH 8.0). The mixture is stirred. After 1 hour the complex of CLA and lead which forms is extracted with hexane. The aqueous portion is found to be free of lead ions.

EXAMPLE 6

Preparation of CLA Derivatives

CLA methyl and ethyl esters were prepared from the free acid form using boron trifluoride methanol according to the AOCS method Ce2-66 (1973). The PTAD derivative of CLA methyl ester was prepared according to the method of Young, et al., Anal. Chem (1987) 59, 1954–1957 after methylation of CLA. We have observed that mouse liver cells containing esterified CLA appear to chelate iron, thereby reducing iron-mediated oxidation.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The preferred pharmaceutical compositions of CLA contain a non-toxic salt of the CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

It will be readily apparent to those skilled in the art that a number of modifications or changes may be made without departing from the spirit and scope of the present invention. Therefore, the invention is only to be limited by the claims.

We claim:

1. A method of chelating metal ions in a solution which comprises adding to a solution containing metal ions an effective amount of a member selected from at least one conjugated linoleic acid, the methyl ester thereof, the ethyl ester thereof and non-toxic salts thereof to chelate the metal ions.

2. A method of claim 1 in which the solution is a body fluid of an animal.

3. A method of claim 1 in which the metal is iron.

4. A method of claim 1 in which the metal is lead.

5. A method of chelating metal ions in a solution which contains metal ions which comprises adding to said solution sufficient amounts of linoleic acid and a protein capable of reacting with the linoleic acid to form conjugated linoleic acids and then intimately mixing the solution at a temperature up to about 85° C. so that conjugated linoleic acids are formed which chelate the metal ions.

6. A method of chelating metal ions in an animal in need thereof which comprises administering to said animal a safe and effective amount of a member selected from at least one conjugated linoleic acid, the methyl ester thereof, the ethyl ester thereof and a non-toxic salt thereof to chelate said metal ions.

* * * * *